(12) United States Patent
Gassler

(10) Patent No.: US 11,065,112 B2
(45) Date of Patent: Jul. 20, 2021

(54) FRAME WITH INTEGRAL SEWING CUFF FOR PROSTHETIC VALVES

(71) Applicant: W. L. Gore & Associates, Inc., Newark, DE (US)

(72) Inventor: Paul D. Gassler, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 37 days.

(21) Appl. No.: 16/394,149

(22) Filed: Apr. 25, 2019

(65) Prior Publication Data

US 2019/0247185 A1    Aug. 15, 2019

Related U.S. Application Data

(62) Division of application No. 15/502,871, filed as application No. PCT/US2015/045002 on Aug. 13, 2015, now Pat. No. 10,314,697.

(60) Provisional application No. 62/038,727, filed on Aug. 18, 2014.

(51) Int. Cl.
*A61F 2/24* (2006.01)

(52) U.S. Cl.
CPC .......... *A61F 2/2415* (2013.01); *A61F 2/2409* (2013.01); *A61F 2210/0076* (2013.01); *A61F 2250/007* (2013.01)

(58) Field of Classification Search
CPC ...................................................... C08L 27/18
See application file for complete search history.

(56) References Cited

U.S. PATENT DOCUMENTS

| | | |
|---|---|---|
| 654,799 A | 7/1900 | Levett |
| 3,953,566 A | 4/1976 | Gore |
| 4,178,639 A | 12/1979 | Bokros |
| 4,222,126 A | 9/1980 | Boretos et al. |
| 4,265,694 A | 5/1981 | Boretos et al. |
| 4,340,091 A | 7/1982 | Skelton et al. |
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 5,123,918 A | 6/1992 | Perrier et al. |
| 5,163,955 A | 11/1992 | Love et al. |
| 5,415,667 A | 5/1995 | Frater |

(Continued)

FOREIGN PATENT DOCUMENTS

| | | |
|---|---|---|
| AU | 2013363172 A1 | 7/2015 |
| CA | 2878691 A1 | 1/2014 |

(Continued)

OTHER PUBLICATIONS

International Search Report and Written Opinion received for PCT Patent Application No. PCT/US15/50113, dated Nov. 24, 2015, 14 pages.

(Continued)

*Primary Examiner* — Yashita Sharma

(57) ABSTRACT

Described embodiments are related to a prosthetic valve for surgical placement with a sewing cuff durably attached to a frame. The durability of the attachment is accomplished by sandwiching a fabric between the frame and a composite material. The fabric extends beyond the frame base to form a sewing cuff that is integral to a frame assembly. The sewing cuff facilitates tissue ingrowth while tissue ingrowth is discouraged elsewhere around the frame.

8 Claims, 9 Drawing Sheets

(56) References Cited

U.S. PATENT DOCUMENTS

| | | |
|---|---|---|
| 5,469,868 A | 11/1995 | Reger |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,708,044 A | 1/1998 | Branca |
| 5,928,281 A | 7/1999 | Van Le Huynh et al. |
| 5,935,163 A | 8/1999 | Gabbay |
| 5,944,654 A | 8/1999 | Crawford |
| 6,019,785 A | 2/2000 | Strecker |
| 6,086,612 A | 7/2000 | Jansen |
| 6,117,169 A | 9/2000 | Moe |
| 6,129,758 A | 10/2000 | Love |
| 6,171,335 B1 | 1/2001 | Wheatley et al. |
| 6,174,331 B1 | 1/2001 | Moe et al. |
| 6,197,143 B1 | 3/2001 | Bodnar |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,454,798 B1 | 9/2002 | Moe |
| 6,454,799 B1 | 9/2002 | Schreck |
| 6,461,382 B1 | 10/2002 | Cao |
| 6,482,228 B1 | 11/2002 | Norred |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,645,244 B2 | 11/2003 | Shu et al. |
| 6,666,885 B2 | 12/2003 | Moe |
| 6,726,715 B2 | 4/2004 | Sutherland |
| 6,730,118 B2 | 5/2004 | Spenser et al. |
| 6,755,857 B2 | 6/2004 | Peterson et al. |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,803,186 B1 | 9/2010 | Li et al. |
| 7,879,085 B2 | 2/2011 | Sowinski et al. |
| 7,914,569 B2 | 3/2011 | Nguyen et al. |
| 7,967,853 B2 | 6/2011 | Eidenschink et al. |
| 7,993,394 B2 | 8/2011 | Hariton et al. |
| 8,062,359 B2 | 11/2011 | Marquez et al. |
| 8,092,523 B2 | 1/2012 | Li et al. |
| 8,167,935 B2 | 5/2012 | McGuckin, Jr. et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,568,475 B2 | 10/2013 | Nguyen et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,154 B2 | 5/2014 | Alkhatib |
| 8,784,481 B2 | 7/2014 | Alkhatib et al. |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,101,469 B2 | 8/2015 | Bruchman et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,283,072 B2 | 3/2016 | Bruchman et al. |
| 9,314,355 B2 | 4/2016 | Styrc et al. |
| 9,375,308 B2 | 6/2016 | Norris |
| 9,393,110 B2 | 7/2016 | Levi et al. |
| 9,398,952 B2 | 7/2016 | Bruchman et al. |
| 9,504,565 B2 | 11/2016 | Armstrong |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,737,398 B2 | 8/2017 | Bruchman et al. |
| 9,743,932 B2 | 8/2017 | Amplatz et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,855,141 B2 | 1/2018 | Dienno et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,639,144 B2 | 5/2020 | Bruchman et al. |
| 10,660,745 B2 | 5/2020 | Bruchman et al. |
| 2002/0045936 A1 | 4/2002 | Moe |
| 2002/0055773 A1 | 5/2002 | Campbell et al. |
| 2002/0082687 A1 | 6/2002 | Moe |
| 2002/0133226 A1 | 9/2002 | Marquez et al. |
| 2002/0183840 A1 | 12/2002 | Lapeyre et al. |
| 2002/0198594 A1 | 12/2002 | Schreck |
| 2003/0027332 A1 | 2/2003 | Lafrance et al. |
| 2003/0055496 A1 | 3/2003 | Cai et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0229394 A1 | 12/2003 | Ogle et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0176839 A1 | 9/2004 | Van Huynh et al. |
| 2004/0243222 A1 | 12/2004 | Osborne et al. |
| 2004/0260393 A1 | 12/2004 | Rahdert et al. |
| 2005/0027348 A1 | 2/2005 | Case et al. |
| 2005/0119722 A1 | 6/2005 | Styrc et al. |
| 2005/0137682 A1 | 6/2005 | Justino |
| 2005/0261765 A1 | 11/2005 | Liddicoat |
| 2006/0008497 A1 | 1/2006 | Gabbay |
| 2006/0041091 A1 | 2/2006 | Chang et al. |
| 2006/0122693 A1 | 6/2006 | Biadillah et al. |
| 2006/0154365 A1 | 7/2006 | Ratcliffe et al. |
| 2006/0229719 A1 | 10/2006 | Marquez et al. |
| 2006/0265053 A1 | 11/2006 | Hunt |
| 2006/0276813 A1 | 12/2006 | Greenberg |
| 2006/0282162 A1 | 12/2006 | Nguyen et al. |
| 2006/0290027 A1 | 12/2006 | O'Connor et al. |
| 2007/0010876 A1 | 1/2007 | Salahieh et al. |

(56) References Cited

U.S. PATENT DOCUMENTS

| | | |
|---|---|---|
| 2007/0021826 A1 | 1/2007 | Case et al. |
| 2007/0118210 A1 | 5/2007 | Pinchuk |
| 2007/0207186 A1 | 9/2007 | Scanlon et al. |
| 2008/0009940 A1 | 1/2008 | Cribier |
| 2008/0026190 A1 | 1/2008 | King et al. |
| 2008/0039934 A1 | 2/2008 | Styrc |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0287305 A1 | 11/2009 | Amalaha |
| 2009/0292350 A1 | 11/2009 | Eberhardt et al. |
| 2010/0023114 A1 | 1/2010 | Chambers et al. |
| 2010/0036021 A1 | 2/2010 | Lee et al. |
| 2010/0049294 A1 | 2/2010 | Zukowski et al. |
| 2010/0082094 A1 | 4/2010 | Quadri et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0262231 A1 | 10/2010 | Tuval et al. |
| 2010/0298931 A1 | 11/2010 | Quadri et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0253453 A1 | 10/2012 | Bruchman et al. |
| 2012/0290082 A1 | 11/2012 | Quint et al. |
| 2012/0323315 A1 | 12/2012 | Bruchman et al. |
| 2013/0018456 A1 | 1/2013 | Li et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0163671 A1 | 6/2014 | Bruchman et al. |
| 2014/0163673 A1 | 6/2014 | Bruchman et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0194968 A1 | 7/2014 | Zukowski |
| 2014/0236289 A1 | 8/2014 | Alkhatib |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0224231 A1 | 8/2015 | Bruchman et al. |
| 2015/0245910 A1 | 9/2015 | Righini et al. |
| 2015/0366663 A1 | 12/2015 | Bruchman et al. |
| 2015/0366664 A1 | 12/2015 | Guttenberg et al. |
| 2016/0001469 A1 | 1/2016 | Baccereti et al. |
| 2016/0074161 A1 | 3/2016 | Bennett |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0095330 A1 | 4/2017 | Malewicz et al. |
| 2017/0128199 A1 | 5/2017 | Gurovich et al. |
| 2017/0156859 A1 | 6/2017 | Chang et al. |
| 2017/0165067 A1 | 6/2017 | Barajas-Torres et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0125646 A1 | 5/2018 | Bruchman et al. |
| 2018/0221144 A1 | 8/2018 | Bruchman et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0237505 A1 | 7/2020 | Bruchman et al. |

(56) References Cited

U.S. PATENT DOCUMENTS

2020/0246137 A1 8/2020 Bruchman et al.
2020/0276014 A1 9/2020 Burkart et al.

FOREIGN PATENT DOCUMENTS

| | | |
|---|---|---|
| CA | 2964546 A1 | 1/2014 |
| CA | 2960034 A1 | 3/2016 |
| CN | 101057796 A | 10/2007 |
| CN | 101091675 A | 12/2007 |
| CN | 101374477 A | 2/2009 |
| CN | 102119013 A | 7/2011 |
| CN | 102438546 A | 5/2012 |
| CN | 102573703 A | 7/2012 |
| CN | 102652694 A | 9/2012 |
| CN | 102764169 A | 11/2012 |
| CN | 102791223 A | 11/2012 |
| CN | 104487023 A | 4/2015 |
| CN | 104507417 A | 4/2015 |
| DE | 212013000104 U1 | 11/2014 |
| EP | 1318775 B1 | 6/2003 |
| EP | 1395205 B1 | 7/2008 |
| EP | 2359774 B1 | 8/2011 |
| EP | 2400923 A1 | 1/2012 |
| EP | 2591100 A2 | 5/2013 |
| EP | 3142608 A1 | 3/2017 |
| FR | 2591100 A1 | 6/1987 |
| GB | 2312485 A | 10/1997 |
| GB | 2513194 A | 10/2014 |
| JP | 44-032400 | 12/1969 |
| JP | 196932400 B | 12/1969 |
| JP | 10-507097 A | 7/1998 |
| JP | 2000511459 A | 9/2000 |
| JP | 2000513248 A | 10/2000 |
| JP | 2001-508681 A | 7/2001 |
| JP | 2001-511030 A | 8/2001 |
| JP | 2002-541915 A | 12/2002 |
| JP | 2004-510471 A | 4/2004 |
| JP | 2005500101 A | 1/2005 |
| JP | 2005-512611 A | 5/2005 |
| JP | 2007536989 A | 12/2007 |
| JP | 2010-517623 A | 5/2010 |
| JP | 2010-528761 A | 8/2010 |
| JP | 2010536527 A | 12/2010 |
| JP | 2012504031 A | 2/2012 |
| JP | 2012152563 A | 8/2012 |
| JP | 2014517720 A | 7/2014 |
| JP | 2016-501104 A | 1/2016 |
| JP | 6392778 B2 | 9/2018 |
| RU | 2434604 C1 | 11/2011 |
| WO | 1996002212 A1 | 2/1996 |
| WO | 0018333 A1 | 4/2000 |
| WO | 2000062716 A1 | 10/2000 |
| WO | 0128453 A2 | 4/2001 |
| WO | 02/07795 A2 | 1/2002 |
| WO | 2002024118 A1 | 3/2002 |
| WO | 2002024119 A1 | 3/2002 |
| WO | 02/47468 A1 | 6/2002 |
| WO | 2002045933 A2 | 6/2002 |
| WO | 2002100301 A1 | 12/2002 |
| WO | 2003007795 A2 | 1/2003 |
| WO | 2003047468 A1 | 6/2003 |
| WO | 03090834 A2 | 11/2003 |
| WO | 2005112827 A2 | 12/2005 |
| WO | 2006108090 A2 | 10/2006 |
| WO | 2007/016251 A2 | 2/2007 |
| WO | 2008/091589 A1 | 7/2008 |
| WO | 2008097589 A1 | 8/2008 |
| WO | 2008097592 A2 | 8/2008 |
| WO | 2009029199 A1 | 3/2009 |
| WO | 2009045332 A2 | 4/2009 |
| WO | 2010037141 A1 | 4/2010 |
| WO | 2010/086460 A1 | 8/2010 |
| WO | 2010057262 A8 | 6/2011 |
| WO | 2011109450 A2 | 9/2011 |
| WO | 2011109801 A2 | 9/2011 |
| WO | 2011112706 A2 | 9/2011 |
| WO | 2012/004460 A2 | 1/2012 |
| WO | 2012040643 A2 | 3/2012 |
| WO | 2012065080 A2 | 5/2012 |
| WO | 2012082952 A2 | 6/2012 |
| WO | 2012110767 A2 | 8/2012 |
| WO | 2012135603 A2 | 10/2012 |
| WO | 2012167131 A1 | 12/2012 |
| WO | 2013096854 A2 | 6/2013 |
| WO | 2014/018189 A2 | 1/2014 |
| WO | 2014018432 A1 | 1/2014 |
| WO | 2014/099150 A1 | 6/2014 |
| WO | 2014/099163 A1 | 6/2014 |
| WO | 2014/099722 A1 | 6/2014 |
| WO | 2014144937 A2 | 9/2014 |
| WO | 2015/045002 A1 | 4/2015 |
| WO | 2015085138 A1 | 6/2015 |
| WO | 2015/171743 A2 | 11/2015 |
| WO | 2015/173794 A1 | 11/2015 |
| WO | 2016028591 A1 | 2/2016 |
| WO | 2016044223 A1 | 3/2016 |
| WO | 2016100913 A1 | 6/2016 |
| WO | 2016/172349 A1 | 10/2016 |
| WO | 2016186909 A1 | 11/2016 |
| WO | 2019/067219 A1 | 4/2019 |
| WO | 2019/067220 A1 | 4/2019 |
| WO | 2019/074607 A1 | 4/2019 |

OTHER PUBLICATIONS

International Search Report and Written Opinion received for PCT Patent Application No. PCT/US2018/050769, dated Nov. 27, 2018, 11 pages.
International Search Report and Written Opinion received for PCT Patent Application No. PCT/US2018/050779, dated Dec. 7, 2018, 14 pages.
Priority Document for U.S. Appl. No. 61/739,721, received by the International Bureau Jan. 3, 2014, 1 page.
Application Data Sheet, Drawings, Specification, Claims, and Abstract filed under U.S. Appl. No. 13/843,196 on Mar. 15, 2013, 52 pages.
European Search Report and Search Opinion Received for EP Application No. 18205790.1, dated Apr. 4, 2019, 7 pages.
European Search Report and Search Opinion Received for EP Application No. 15186981.5, dated Feb. 10, 2016, 5 pages.
European Search Report and Search Opinion Received for EP Application No. 17167842.8, dated Jun. 21, 2017, 5 pages.
European Search Report and Search Opinion Received for EP Application No. 17176507.6, dated Sep. 6, 2017, 5 pages.
European Search Report and Search Opinion Received for EP Application No. 17187595.8, dated Dec. 4, 2017, 5 pages.
European Search Report and Search Opinion Received for EP Application No. 17194473.9, dated Feb. 26, 2018, 9 pages.
European Search Report from EP16196687.4, dated Nov. 21, 2017, 5 pages.
International Preliminary Report on Patentability from PCT/US2015/045002, dated Mar. 2, 2017, 11 pages.
International Preliminary Report on Patentability received for PCT Patent Application No. PCT/US13/68390, dated Jul. 2, 2015, 12 pages.
International Preliminary Report on Patentability received for PCT Patent Application No. PCT/US13/71632, dated Jul. 2, 2015, 11 pages.
International Preliminary Report on Patentability received for PCT Patent Application No. PCT/US13/74962, dated Jul. 2, 2015, 9 pages.
International Preliminary Report on Patentability received for PCT Patent Application No. PCT/US13/75274, dated Jul. 2, 2015, 8 pages.
International Preliminary Report on Patentability received for PCT Patent Application No. PCT/US13/75380, dated Jul. 2, 2015, 7 pages.
International Preliminary Report on Patentability received for PCT Patent Application No. PCT/US13/76504, dated Jul. 2, 2015, 13 pages.

(56) References Cited

OTHER PUBLICATIONS

International Preliminary Report on Patentability received for PCT Patent Application No. PCT/US13/76688, dated Jul. 2, 2015, 12 pages.
International Preliminary Report on Patentability received for PCT Patent Application No. PCT/US14/68727, dated Jun. 16, 2016, 9 pages.
International Preliminary Report on Patentability received for PCT Patent Application No. PCT/US2013/046389, dated Feb. 5, 2015, 13 pages.
International Preliminary Report on Patentability received for PCT Patent Application No. PCT/US2013/051431, dated Feb. 5, 2015, 9 pages.
International Search Report and Written Opinion for PCT/US2014/068727 dated Mar. 2, 2015, corresponding to U.S. Appl. No. 14/561,148; 6 pages.
International Search Report and Written Opinion for PCT/US2014/068727 dated Mar. 2, 2015, corresponding to U.S. Appl. No. 14/561,148; 12 pages.
International Search Report and Written Opinion for PCT/US2015/050113, dated Nov. 24, 2015, 14 pages.
International Search Report and Written Opinion from PCT/US2018/053278, dated Dec. 19, 2018, 12 pages.
International Search Report and Written Opinion issued in PCT/US2018/050766, dated Mar. 11, 2019, 16 pages.
International Search Report and Written Opinion received for PCT Patent Application No. PCT/US2015/045002, dated Dec. 17, 2015, 13 pages.
International Search Report for PCT/US2013/046389 dated Jan. 21, 2014, corresponding to U.S. Appl. No. 13/797,633; 18 pages.
International Search Report for PCT/US2013/051431 dated Jan. 20, 2014, corresponding to U.S. Appl. No. 13/797,526; 6 pages.
International Search Report for PCT/US2013/068390 dated Apr. 29, 2014, corresponding to U.S. Appl. No. 13/835,988, 7 pages.
International Search Report for PCT/US2013/068780 dated Feb. 27, 2014, corresponding to U.S. Appl. No. 13/869,878, 4 pages.
International Search Report for PCT/US2013/071632 dated Apr. 28, 2014, corresponding to U.S. Appl. No. 13/841,334, 6 pages.
International Search Report for PCT/US2013/074962 dated Feb. 27, 2014, 4 pages.
International Search Report for PCT/US2013/075274 dated Feb. 27, 2014, corresponding to U.S. Appl. No. 13/843,196, I pages.
International Search Report for PCT/US2013/075274 dated Feb. 27, 2014, corresponding to U.S. Appl. No. 13/843,196, 5 pages.
International Search Report for PCT/US2013/075275 dated Jun. 11, 2014, corresponding to U.S. Appl. No. 13/843,196, 5 pages.
International Search Report for PCT/US2013/075380 dated Mar. 6, 2014, 5 pages.
International Search Report for PCT/US2013/076504 dated Apr. 28, 2014, corresponding to U.S. Appl. No. 14/133,491, 7 pages.
International Search Report for PCT/US2013/076688 dated Feb. 27, 2014, 5 pages.
Mano Thubrikar, "The Aortic Valve", Chapter 1: Geometry of the Aortic Valve, CRC Press, Inc., Informa Healthcare, 2011, 40 pages.
Norman E. Clough. Introducing a New Family of GORE (Trademark) ePTFE Fibers (2007).
Opposition from EP16196687.4, mailed on Dec. 12, 2019, 38 pages.
Opposition from EP17187595.8, filed Sep. 12, 2019, 50 pages.
Clough, Norman E. Introducing a New Family of GORE ePTFE Fibers (2007), pp. 1-10.
Extended European Search Report issued in EP Application No. 18204192.1, dated May 29, 2019.
International Preliminary Report on Patentability issued in PCT/US2017/047174, dated Mar. 7, 2019, 9 pages.
International Search Report and Written Opinion from PCT/US2018/050768, dated Dec. 17, 2018, 12 pages.
International Search Report and Written Opinion from PCT/US2018/050786 dated Dec. 14, 2018, 13 pages.
International Search Report and Written Opinion issued in PCT/US2018/050764, dated Nov. 23, 2018, 13 pages.
International Search Report and Written Opinion issued in PCT/US2018/050778, dated Nov. 29, 2018, 11 pages.
International Search Report and Written Opinion received for PCT Application No. PCT/US2020/020550, dated Jun. 9, 2020, 12 pages.

FRAME WITH INTEGRAL SEWING CUFF FOR PROSTHETIC VALVES

CROSS REFERENCE TO RELATED APPLICATIONS

This application is a divisional of U.S. application Ser. No. 15/502,871, filed Feb. 9, 2017, which is a national phase application of PCT Application No. PCT/US2015/045002, internationally filed Aug. 13, 2015, which claims the benefit of U.S. provisional Application No. 62/038,727, filed Aug. 18, 2014, all of which are herein incorporated by reference in their entireties.

FIELD

The present disclosure relates generally to prosthetic valves, and more specifically, a frame with integral sewing cuff-type prosthetic valve devices, systems, and methods.

BACKGROUND

Prosthetic heart valves have been developed that attempt to mimic the function and performance of a native valve. The prosthetic valve is typically attached to a human heart with sutures via a sewing cuff, or some other mechanical attachment means (e.g., staples).

Sewing cuffs generally comprise a toroidal member that is attached to the periphery of a prosthetic valve body to form a structure for anchoring sutures to the annulus of the heart during implantation of the prosthetic valve. Sewing cuffs commonly comprise a cloth material, such as polyester, and may also comprise a filler material such as Teflon felt or Dacron cloth. The sewing cuff may be coupled to a peripheral groove located on a lower end of the valve body by circumferential cinch-like sutures, or may be mechanically captured adjacent to a stiffening ring.

SUMMARY

Described embodiments are directed to an apparatus, system, and methods for valve replacement, such as cardiac valve replacement. More specifically, described embodiments are directed toward a frame assembly including an integral sewing cuff for use in a prosthetic valve.

In accordance with an embodiment, a prosthetic valve comprises a frame. The frame has a tubular shape with a frame inside surface and a frame outside surface opposite the frame inside surface. The prosthetic valve further comprises a fabric with fabric pores having a fabric frame portion and a sewing cuff opposite the fabric frame portion. The fabric frame portion has an elastomer present in the fabric pores. The fabric frame portion is coupled to the frame. The sewing cuff extends from the frame. A composite material is coupled to at least a portion of the fabric frame portion with the fabric frame portion disposed between the frame and the composite material. Leaflets are coupled to the frame.

In accordance with an embodiment, a prosthetic valve frame assembly comprises a frame. The frame has a tubular shape with a frame inside surface and a frame outside surface opposite the frame inside surface. The prosthetic valve further comprises a fabric with fabric pores having a fabric frame portion and a sewing cuff opposite the fabric frame portion. The fabric frame portion has an elastomer present in the fabric pores. The fabric frame portion is coupled to the frame. The sewing cuff extends from the frame. A composite material is coupled to at least a portion of the fabric frame portion with the fabric frame portion disposed between the frame and the composite material.

In accordance with an embodiment of method of making a frame assembly for a prosthetic valve, a first layer of film is wrapped into a tubular form about a mandrel. A fabric having a tubular shape is provided. The fabric is partially placed over the first layer of film. A frame having a tubular shape is provided. The frame has a frame inside surface and a frame outside surface and defines a frame base and a plurality of leaflet windows. The frame is placed over the fabric that is over the first layer of film with the frame inside surface in contact with the fabric. The fabric is everted over the frame base and over the frame outside surface in contact with the frame outside surface defining a fold in the fabric with the fold extending from the frame base, the fold defining a sewing cuff. A second layer of film is wrapped over the fabric that is over the frame outside surface. The first layer of film and the second layer of film are coupled to each other, to the fabric, and to the frame.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

DEFINITIONS

Figure 1A:
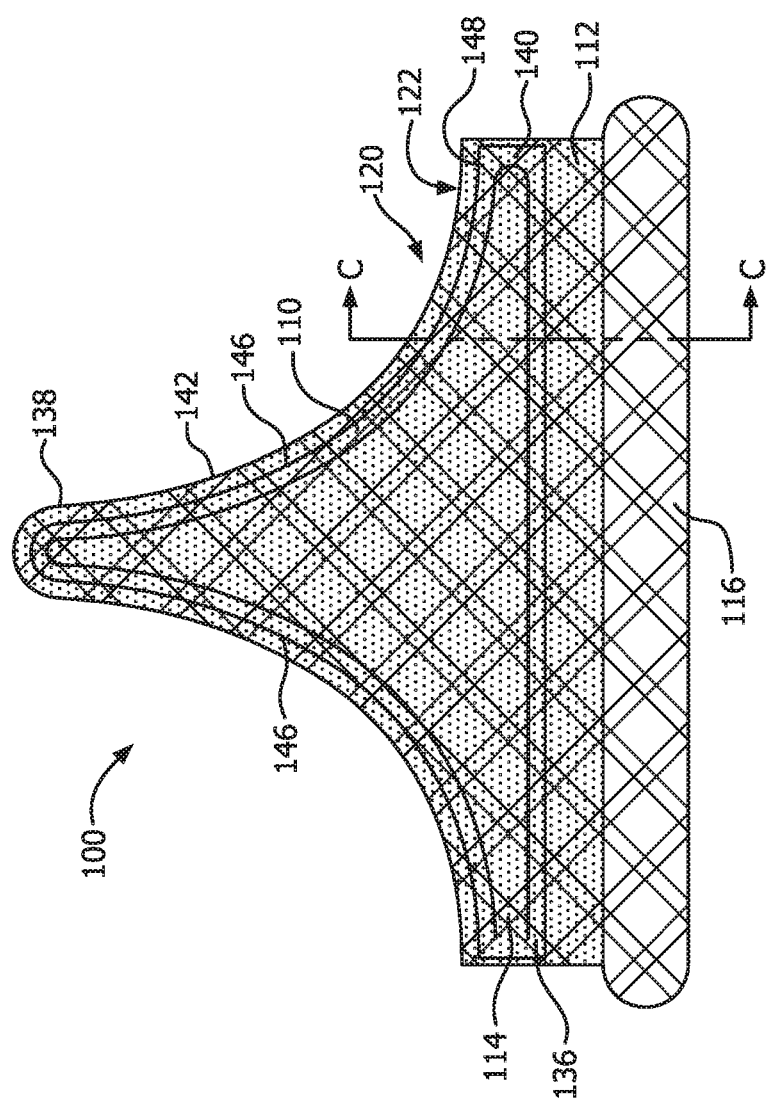
FIG. 1A is a side view of an embodiment of a prosthetic valve.

The term leaflet as used herein in the context of prosthetic valves is a component of a one-way valve wherein the leaflet is operable to move between an open and closed position under the influence of a pressure differential. In an open position, the leaflet allows blood to flow through the prosthetic valve. In a closed position, the leaflet blocks retrograde flow through the prosthetic valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the prosthetic valve rises above the pressure on the outflow side of the prosthetic valve, the leaflets open and blood flows therethrough. As blood flows through the prosthetic valve into a neighboring chamber or blood vessel, the pressure on the inflow side equalizes with the pressure on the outflow side. As the pressure on the outflow side of the prosthetic valve raises above the blood pressure on the inflow side of the prosthetic valve, the leaflet returns to the closed position preventing retrograde flow of blood through the prosthetic valve. Leaflets may be comprised of biological tissue, such as bovine pericardium, or synthetic, biocompatible materials sufficiently compliant and flexible, such as a biocompatible polymer.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be present within a porous structure of the membrane, coated on one or both sides of the membrane, or a combination of coated on and imbibed.

The term imbibed as used herein refers to the presence of material in the pores of a film. The process of imbibing as used herein refers to the means for depositing a material into the pores of the film. Means for imbibing may include, but are not limited to, printing, soaking, or any other suitable means for delivering materials into the pores.

The term laminate as used herein refers to an article comprising multiple layers of membrane, composite material, or other materials, such as elastomer, and combinations thereof, that are coupled together.

The term film as used herein refers to one or more of the membrane, composite material, or laminate.

The term pores generally refers to void space that may be found in a material. Pores that are found in a fabric is referred to as fabric pores. Pores that are found in fluoropolymer membrane are referred to as fluoropolymer membrane pores. Pores also refers to void spaces in which another material may be present.

The term biocompatible material as used herein generically refers to a film or a biological material, such as, but not limited to, bovine pericardium.

The term leaflet window is defined as that space that a frame defines, and from which a leaflet extends. The leaflet may extend from frame elements or adjacent to frame elements and spaced apart therefrom.

The terms native valve orifice and tissue orifice refer to an anatomical structure into which a prosthetic valve may be placed. Such anatomical structure includes, but is not limited to, a location wherein a cardiac valve may or may not have been surgically removed. It is understood that other anatomical structures that may receive a prosthetic valve include, but are not limited to, veins, arteries, ducts and shunts. Although reference is made herein to replacing a native valve with a prosthetic valve, it is understood and appreciated that a valve orifice or implant site may also refer to a location in a synthetic or biological conduit that may receive a prosthetic valve for a particular purpose, and therefore the scope of the embodiments provided herein is not limited to native valve replacement.

The term couple as used herein is used synonymously with join, connect, attach, adhere, affix, or bond, whether directly or indirectly, and whether permanently or temporarily.

DETAILED DESCRIPTION

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any prosthetic valve or mechanism of similar structure and/or function. Furthermore, embodiments within the scope of this disclosure can be applied in non-cardiac applications.

Embodiments herein include various apparatus, systems, and methods for a prosthetic valve suitable for surgical placement, such as, but not limited to, cardiac valve replacement. The prosthetic valve is operable as a one-way valve wherein the prosthetic valve defines a valve orifice into which leaflets open to permit flow and close so as to occlude the valve orifice and prevent flow in response to differential fluid pressure.

Embodiments provided herein are related to a prosthetic valve with an integral sewing cuff that is durably attached to a frame and suitable for surgical placement. The durability of the attachment of the sewing cuff is accomplished by sandwiching a fabric between a frame and a composite material, in accordance with an embodiment. The fabric extends beyond a frame base to form a sewing cuff that is integral to the frame assembly.

As will be described below, in accordance with an embodiment, the sewing cuff facilitates tissue ingrowth while tissue ingrowth is discouraged elsewhere around the frame.

Prosthetic Valve

Figure 1B:
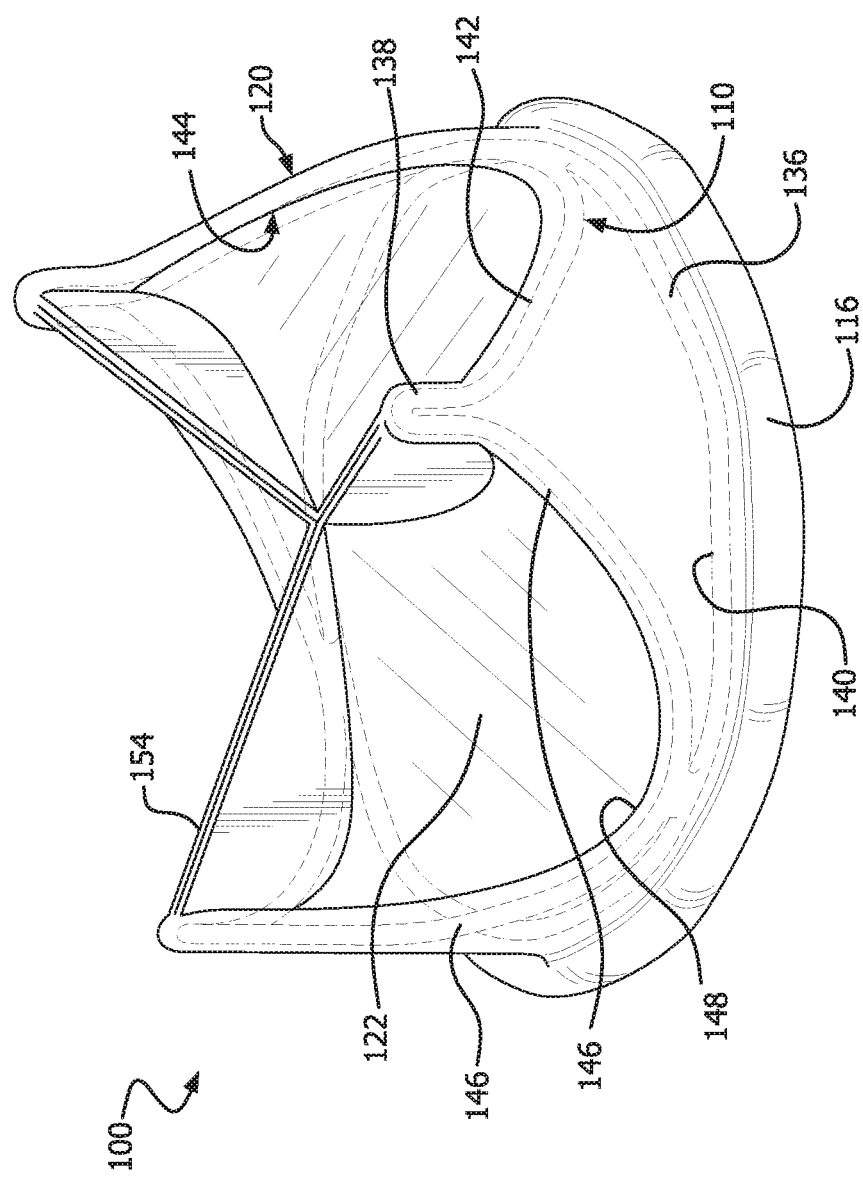
FIG. 1B is a perspective view of the embodiment of the prosthetic valve of FIG. 1A.
Figure 1C:
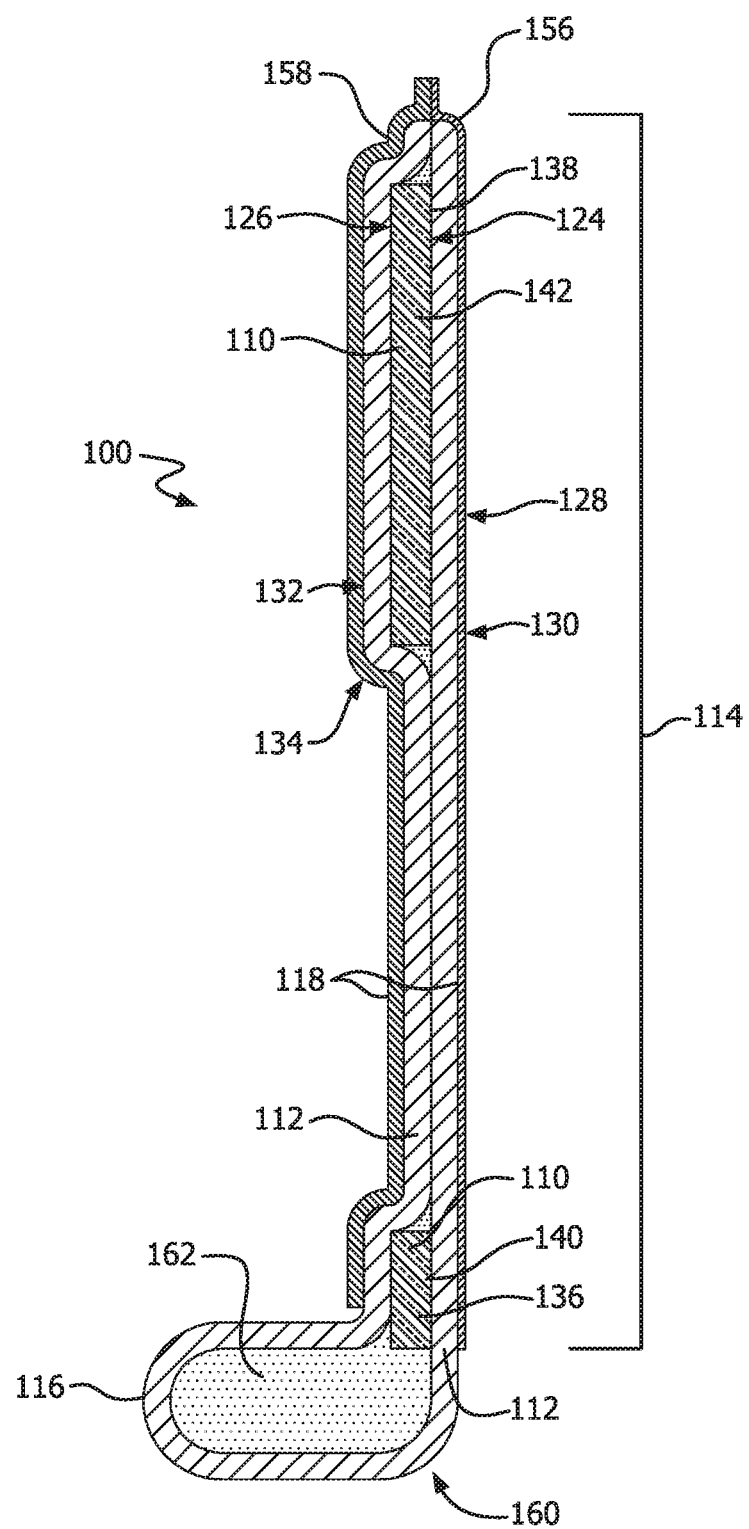
FIG. 1C is an axial cross-sectional view along line C-C of the embodiment of the prosthetic valve of FIG. 1A.

FIG. 1A is a side view of a prosthetic valve 100, in accordance with an embodiment. FIG. 1B is a perspective view of the prosthetic valve 100 of FIG. 1A, and FIG. 1C is an axial cross-sectional view of a portion of the prosthetic valve 100 of FIG. 1A along cut-line C-C. The prosthetic valve 100 comprises leaflets 122 and a frame assembly 120 with sewing cuff 116. The frame assembly 120 with sewing cuff 116 comprises a frame 110 with a frame inside surface 124 and a frame outside surface 126, a fabric 112 with fabric pores that is coupled to the frame 110 defining a fabric frame portion 114 that extends beyond the frame 110 to form a sewing cuff 116, a composite material 118 coupled to at least a portion of the fabric frame portion 114 such that the fabric 112 is between the composite material 118 and the frame 110.

As shown in FIG. 1C, the fabric 112 and composite material 118 are coupled to both the frame inside surface 124 and frame outside surface 126 of the frame 110 thereby defining an inner fabric frame portion 128, an inner composite material 130, an outer fabric frame portion 132, and an outer composite material 134. In another embodiment, the fabric 112 and composite material 118 are coupled to only the frame inside surface 124 of the frame 110, defining an inner fabric frame portion 128 and an inner composite material 130. In yet another embodiment, the fabric 112 and composite material 118 are coupled to only the frame outside surface 126 of the frame 110, defining an outer fabric frame portion 132 and an outer composite material 134.

As shown in FIGS. 1A-1C, the composite material 118 may be coupled to substantially all of the fabric frame portion 114, that is, coupled to the frame 110. The composite material 118 may further extend beyond the frame 110 into the leaflet windows 144 to form the leaflets 122. Alternatively, leaflets 122 may be sewn or otherwise coupled to the frame assembly 120.

Frame

Referring to FIGS. 1A-1C, the frame 110 is a tubular member defining a predetermined repeating pattern. The frame 110 comprises a frame first end 136 and a frame second end 138 opposite the frame first end 136. Positioned at the frame first end 136 is the frame base 140. A plurality of spaced apart frame strut elements 142 extend from the frame first end 136 to the frame second end 138 in a predetermined repeating pattern. The frame 110 further comprises a frame outside surface 126 and a frame inside surface 124 opposite the frame outside surface 126, as shown in FIG. 1C.

The frame base 140 and frame strut elements 142 define leaflet windows 144. Each leaflet window 144 includes two leaflet window sides 146 and a leaflet window base 148. As will be described in more detail below, a biocompatible material is disposed over each of the leaflet windows 144 to form a leaflet 122. The leaflet window 144 may define any shape suitable for a particular purpose of an embodiment of a prosthetic valve 100, including, but not limited to a parabolic shape, a trapezoidal shape, and a triangular shape.

The frame 110 may be referred to in a general sense as a stent or a frame. The frame 110 defines any number of features and geometric shapes that facilitate support to the leaflet 122 and provide dimensional stability when implanted.

The frame 110 may comprise a cut tube or wire form, or any other element suitable for the particular purpose. The frame 110 may be etched, cut, laser cut, or stamped from a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework.

The frame 110 can comprise any metallic or polymeric biocompatible material. For example, the frame 110 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Figure 2A:
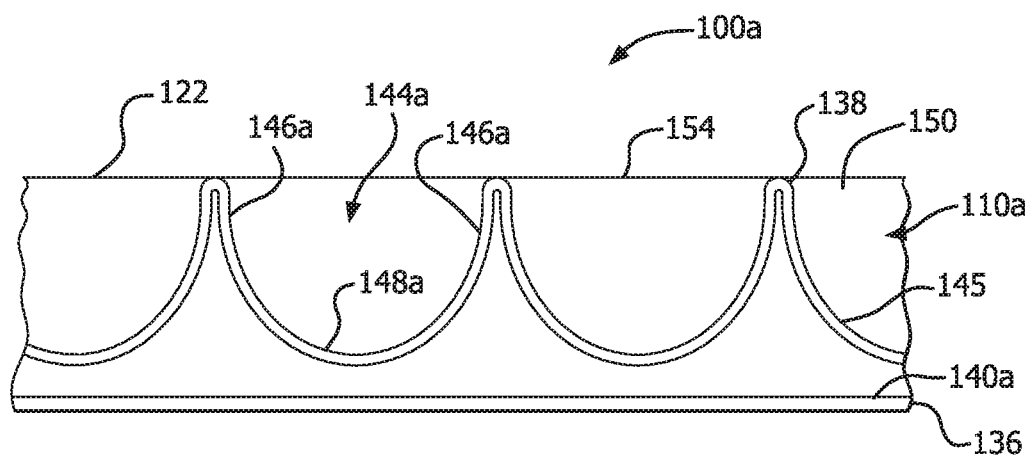
FIG. 2A is a representation of an embodiment of a frame unrolled to a flat orientation.
Figure 2B:
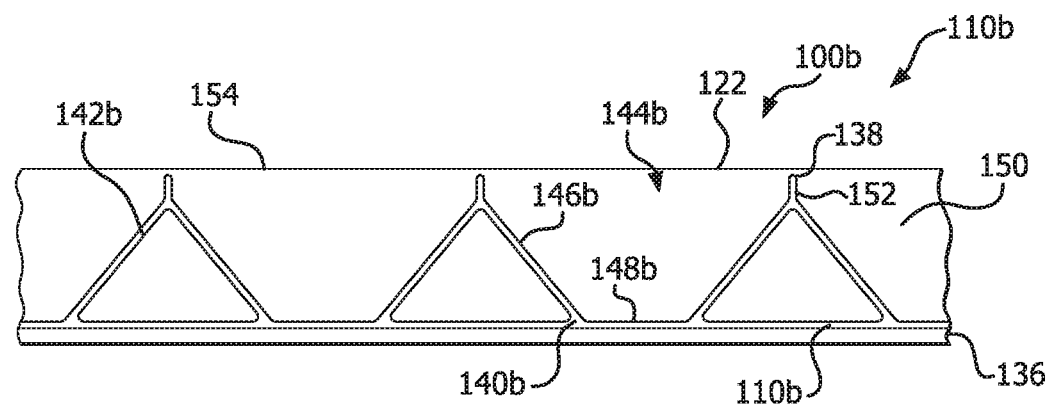
FIG. 2B is a representation of another embodiment of a frame unrolled to a flat orientation.

FIGS. 2A-2B are side views of alternative embodiments of the frame 110a-110b where the frame has been cut longitudinally and laid open to better illustrate the elements of the frame.

FIG. 2A is a representation of an embodiment of a prosthetic valve 100a comprising a frame 110a that has been unrolled to a flat orientation to better illustrate the elements. The frame 110a is formed from a wire 145. The wire 145 is formed into a cylindrical shape that defines a plurality of U-shaped or parabola shaped leaflet windows 144a with leaflet window sides 146a that extend to the frame second end 138 and a leaflet window base 148a that is adjacent to the frame first end 136. The wire 145 further defines the frame base 140b at the frame first end 136.

FIG. 2B is a representation of an embodiment of a prosthetic valve 100b comprising a frame 110b that has been unrolled to a flat orientation to better illustrate the elements. The frame 110b comprises a plurality of spaced apart frame strut elements 142b defining substantially an isosceles triangle interconnected by another frame strut element 142b that defines the frame base 140b and defining leaflet windows 144b. Each leaflet window side 146b is defined by a side of one triangle and a side of an adjacent triangle, and wherein each leaflet window base 148b is defined by a frame strut element 142b that defines a portion of the frame base 140b. The frame second end 138 further comprises posts 152 extending from an apex of the frame strut elements 142b that define each of the isosceles triangles.

It is understood that the frame 110 may comprise any number of leaflet windows 144, and thus leaflets 122, suitable for a particular purpose, in accordance with embodiments. Frames comprising one, two, three or more leaflet windows and corresponding leaflets are anticipated.

Fabric and Sewing Cuff

In accordance with an embodiment of a prosthetic valve 100 suitable for surgical implantation, the prosthetic valve 100 further comprises a sewing cuff 116 about a frame outside surface 126 in accordance with an embodiment, as shown in FIGS. 1A-1C and FIG. 4. The sewing cuff 116 is operable to provide structure that receives suture for coupling the prosthetic valve 100 to the implant site, such as the tissue orifice. The sewing cuff 116 may be located circumferentially around the frame base 140 of the frame 110 or paravalvular, that is, extending axially from the frame base 140.

Referring again to the embodiment of FIG. 1C, a fabric 112 with fabric pores is coupled to the frame inside surface 124 and the frame outside surface 126. Portions of the fabric 112 that are coupled to the frame 110 define fabric frame portions 114. The sewing cuff 116 is formed from fabric 112 material that extends beyond the frame base 140. As shown in FIG. 1C, the fabric 112 defines a fabric first end 156, a fabric second end 158 opposite the fabric first end 156, and a fabric central portion 160 between the fabric first end 156 and the fabric second end 158. The fabric frame portion 114 comprises the fabric first end 156 which is coupled to the frame inside surface 124, and the fabric second end 158 which is coupled to the frame outside surface 126. The fabric central portion 160 comprises the sewing cuff 116, which is defined by a loop or fold of the fabric 112 extending beyond the frame base 140.

In an embodiment, the fabric 112 is coupled to substantially all of the frame inside surface 124 and substantially all of the frame outside surface 126, including the frame base 140 and the frame strut elements 142. In other embodiments the fabric 112 is coupled to a portion of the frame inside surface 124 and/or a portion of the frame outside surface 126. In other embodiments, the fabric 112 is coupled to the frame 110 at the frame base 140 on either the frame inside surface 124 and/or the frame outside surface 126. The fabric 112 may further extend, wholly or partially, into the leaflet windows 144. Extension of the fabric 112 at least partially into the leaflet window 144 may benefit the durability of the leaflet 144 as a reinforcement or a cushion layer between the frame 110 and the leaflet material that is coupled to the leaflet window 144.

In accordance with an embodiments, the fabric frame portion 114 has an elastomer present in the fabric pores of the fabric 112; in contrast, the sewing cuff 116 does not have an elastomer present in the fabric pores of fabric 112. This enables the sewing cuff 116 to be operable to facilitate tissue ingrowth into the fabric pores, but tissue ingrowth is discouraged elsewhere around the frame assembly 120. In another embodiment a predetermined portion of the sewing cuff 116 may have an elastomer present in the fabric pores of the fabric 112 so that tissue ingrowth is facilitated in specific regions of the sewing cuff 116 but not in others.

The sewing cuff 116 and fabric frame portion 114 may comprise any suitable fabric 112, such as, but not limited to, double velour polyester, PTFE, ePTFE, Dacron, or any other biocompatible fabric that does not deteriorate over time. The fabric 112 may be knit, woven, or non-woven. The sewing cuff 116 may further comprise a filler 162 between fabric layers. The filler 162 material may comprise the same material as the fabric 112 or may be any other suitable material, including silicone. The filler 162 may be a bead of material, a base tube rolled into an O-ring, one or more layers of a knit or woven material, wraps of a fiber, or any other suitable form. In some embodiments the filler 162 may be injected through a needle between the layers of the fabric 112 that form the sewing cuff 116 or inserted through a seam in the fabric 112 that is subsequently sewn together. The sewing cuff 116 may be located circumferentially around a perimeter of the frame 110.

In some embodiments the sewing cuff 116 and fabric frame portion 114 are comprised of a single piece of fabric. In other embodiments the sewing cuff 116 and fabric frame portion 114 are comprised of two or more fabric pieces which are coupled together by sewing, use of an adhesive, or any other suitable means.

Leaflet

Referring to FIGS. 1B and 2A-B, each leaflet window 144 is provided with a biocompatible material, such as a film or bovine pericardium, which is coupled to the leaflet window sides 146 and leaflet window base 148 with the biocompatible material defining a leaflet 122. The shape of the leaflets 122 are defined in part by the shape of the leaflet window 144 and the leaflet free edge 154.

Figure 3A:
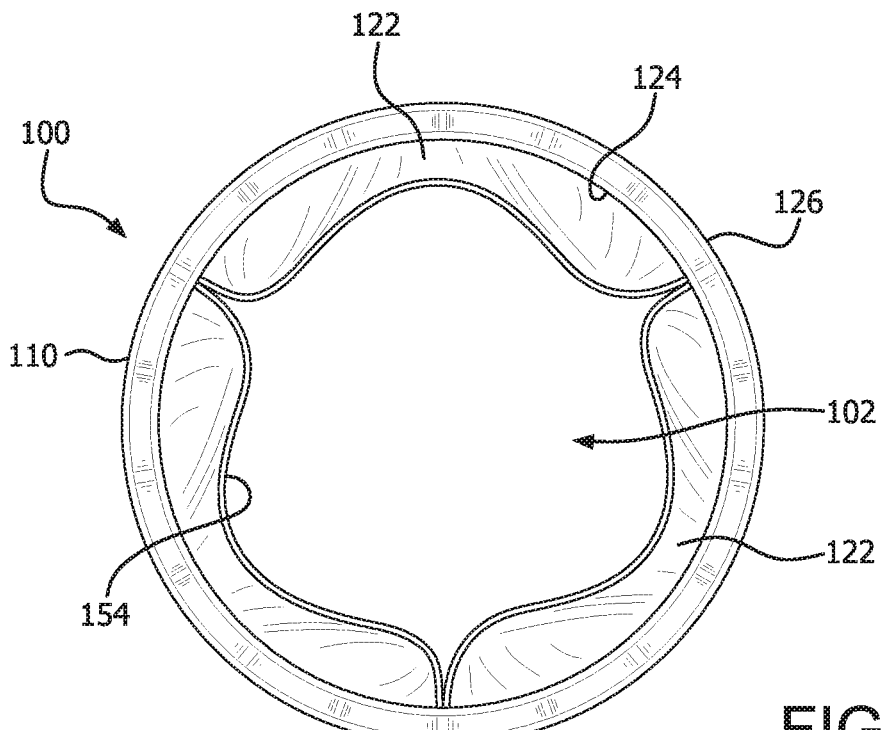
FIG. 3A is an axial or top view of an embodiment of a prosthetic valve in an open configuration.
Figure 3B:
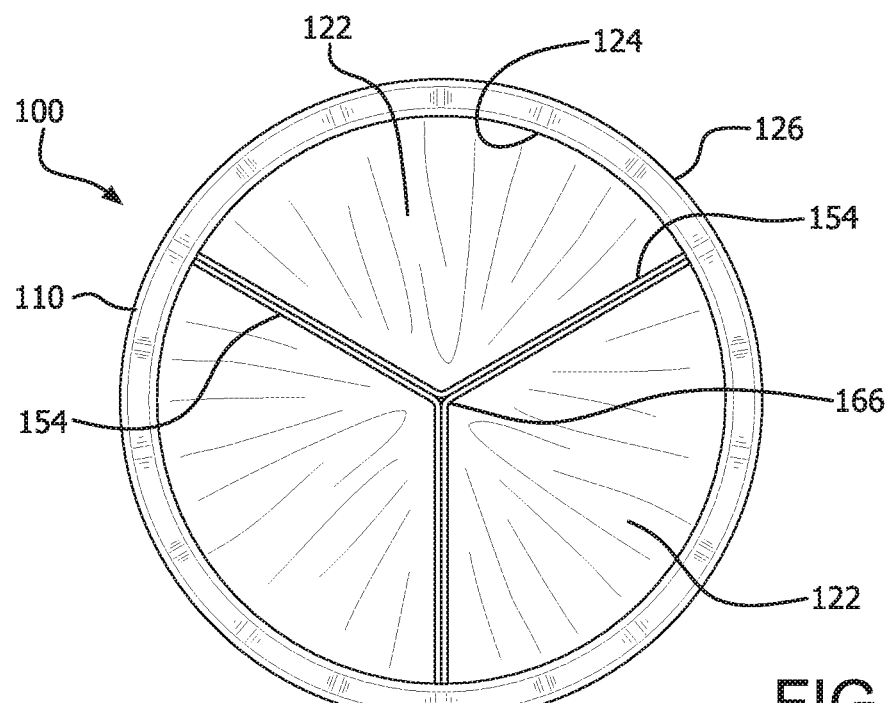
FIG. 3B is an axial or top view of the embodiment of the prosthetic valve of FIG. 3A in a closed configuration.
Figure 4:
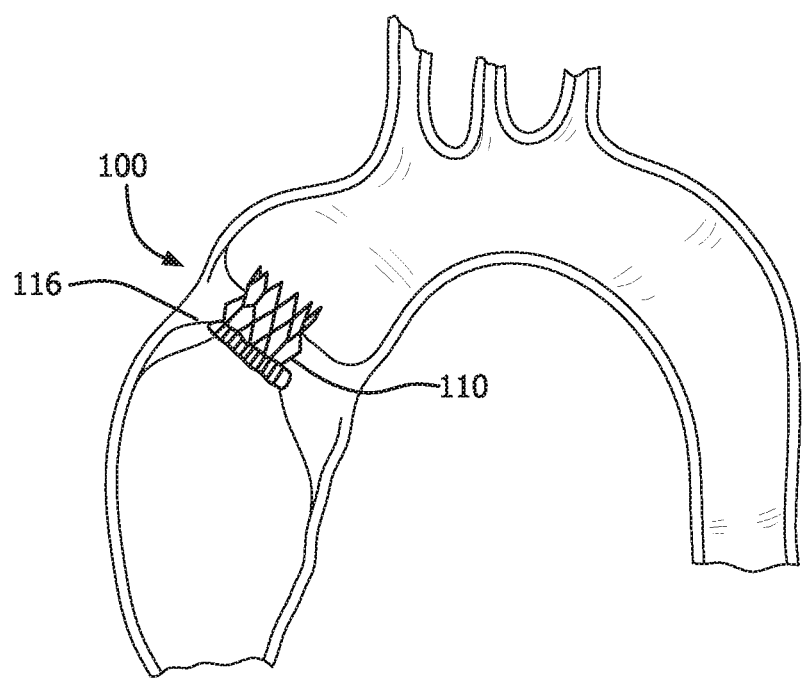
FIG. 4 is a side view of an embodiment of a prosthetic valve within the anatomy.

FIGS. 3A and 3B are top axial views of a prosthetic valve 100 in an open and closed position, respectively. When the leaflets 122 are in a fully open position, the prosthetic valve 100 presents a valve orifice 102 that is substantially circular as shown in FIG. 3A. Fluid flow is permitted through the valve orifice 102 when the leaflets 122 are in an open position. When the leaflets 122 are in a closed position, the prosthetic valve 100 presents a substantially occluded orifice restricting fluid flow.

Film

A film 150 is any sheet-like material that is biologically compatible and configured to couple to the frame 110, in accordance with embodiments. It is understood that the term "film" is used generically for one or more biocompatible materials suitable for a particular purpose.

In accordance with an embodiment, the biocompatible material is a film that is not of a biological source and that is sufficiently flexible and strong for the particular purpose, such as a biocompatible polymer. In an embodiment, the film comprises a biocompatible polymer that is combined with an elastomer, referred to as a composite material.

In an embodiment, the film 150 may be formed from a tubular shape to at least partially cover the frame 110. The film 150 can comprise one or more of a membrane, composite material, or laminate. Details of various types of film 150 are discussed below.

The biocompatible material that makes up the film can comprise any biological tissue or synthetic, biocompatible materials sufficiently compliant and flexible, such as a biocompatible polymer. In an embodiment, the film comprises a biocompatible polymer that is combined with an elastomer, referred to as a composite material. A material according to one embodiment includes a composite material comprising an expanded fluoropolymer membrane, which comprises a plurality of void spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore defining fluoropolymer membrane pores. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

In another embodiment, the expanded fluoropolymer membrane has a microstructure of substantially only fibrils, as is generally taught by U.S. Pat. No. 7,306,729, to Bacino, defining fluoropolymer membrane pores. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5 \times 10^5$ $MPa^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 122 comprises an expanded fluoropolymer membrane having a thickness of about 0.1 μm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the fluoropolymer membrane pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 µm and a mass per area of about 4.1 g/m².

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in the fluoropolymer membrane pores of the at least one fluoropolymer layer. Having elastomer filling the pore volume or present in the fluoropolymer membrane pores reduces the space in which foreign materials can be undesirably incorporated into the composite. An example of such foreign material is calcium that may be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. In another embodiment, the elastomer is Silicone MED-4720, NuSil, Carpinteria, Calif., USA.

As discussed above, the elastomer is combined with the expanded fluoropolymer membrane such that the elastomer occupies the void space or fluoropolymer membrane pores within the expanded fluoropolymer membrane to form a composite material. This filling of the fluoropolymer membrane pores of the expanded fluoropolymer membrane with elastomer can be performed by a variety of methods. In one embodiment, a method of filling the fluoropolymer membrane pores of the expanded fluoropolymer membrane includes the steps of dissolving the elastomer in a solvent suitable to create a solution with a viscosity and surface tension that is appropriate to partially or fully flow into the fluoropolymer membrane pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang et al.

In another embodiment, a method of filling the fluoropolymer membrane pores of the expanded fluoropolymer membrane includes the steps of delivering the filler via a dispersion to partially or fully fill the fluoropolymer membrane pores of the expanded fluoropolymer membrane.

In another embodiment, a method of filling the fluoropolymer membrane pores of the expanded fluoropolymer membrane includes the steps of bringing the porous expanded fluoropolymer membrane into contact with a sheet of the elastomer under conditions of heat and/or pressure that allow elastomer to flow into the fluoropolymer membrane pores of the expanded fluoropolymer membrane.

In another embodiment, a method of filling the fluoropolymer membrane pores of the expanded fluoropolymer membrane includes the steps of polymerizing the elastomer within the fluoropolymer membrane pores of the expanded fluoropolymer membrane by first filling the fluoropolymer membrane pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use as a leaflet include but are not limited to the groups of urethanes, silicones(organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Other Considerations

The prosthetic valve 100 can further comprise a bio-active agent. Bio-active agents can be coated onto a portion or the entirety of the film 150 for controlled release of the agents once the prosthetic valve 100 is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epipodophyllotoxins (i.e. etoposide, teniposide), antibiotics (dactinomycin (actinomycin D), daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Method of Making

Embodiments described herein also pertain to a method of making the embodiments of a prosthetic valve as described herein. In order to make the various embodiments, a cylindrical assembly mandrel 168 can be used. With reference to FIGS. 5, 6A-6C, the assembly mandrel 168 comprises a structural form operable to receive the frame 110 thereon. An embodiment of a method of making a prosthetic valve 100 comprises the steps of coupling the fabric 112 to the frame 110 with a fabric central portion 160 of the fabric 112 extending beyond the frame base 140 that will be used to form the sewing cuff 116 of FIG. 1A; imbibing the fabric frame portion 114 with an elastomer so that the elastomer is present in the fabric pores of the fabric 112 while keeping the fabric central portion 160 of the fabric 112 that will be made into the sewing cuff 116 free of elastomer in the fabric pores of the fabric 112; thermally setting the assembly; coupling a composite material 118 to the fabric frame portion 114 such that the fabric frame portion 114 is between the frame 110 and the composite material 118.

EXAMPLE

A frame assembly 120 with sewing cuff 116 that is integral to the frame assembly 120 was made in the following manner. The following knit fabric was obtained. A 32 TPI, 32ga 2-bar in-lay warp knit was created using 100 denier, round ePTFE fiber (W.L. Gore and Associates, Elkton, Md.). Parallel cuts were made in the knit at 45 degrees relative to the warp direction and hand sewn into a 25 mm diameter tube using CV-4 GORE-TEX Suture (W.L. Gore and Associates, Flagstaff, Ariz.).

Figure 5:
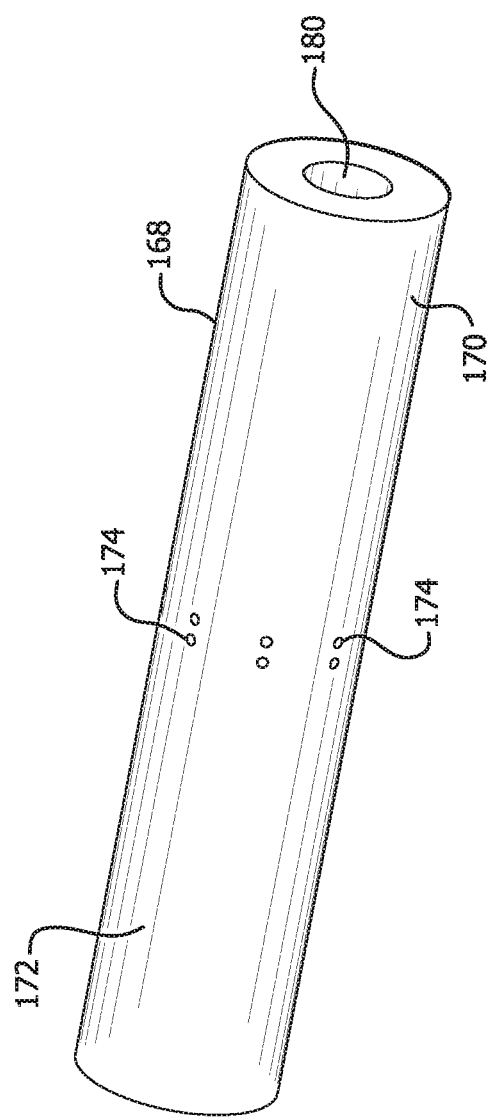
FIG. 5 is a perspective view of an embodiment of an assembly mandrel.

An assembly mandrel 168 was machined from aluminum in a cylindrical shape shown in perspective view in FIG. 5. The assembly mandrel 168 has a first end 170 and an opposing second end 172. Two rows of six 0.5 mm diameter vent holes 174 were drilled into the assembly mandrel 168 as shown in FIG. 5. The vent holes 174 communicate with a vent port 180.

Two layers of a sacrificial composite material comprising polyimide imbibed ePTFE film with a thickness of approximately 0.004 mm were wrapped around assembly mandrel 168. The sacrificial composite material was punctured above the vent holes 174.

Figure 6A:
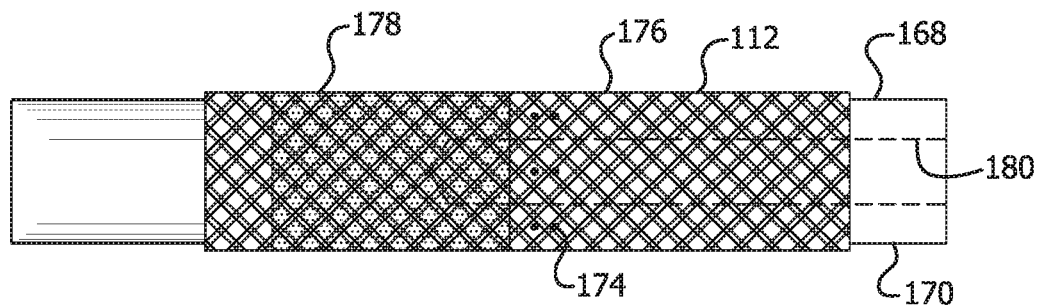
FIG. 6A-F are side views of stages in an example process for making a frame assembly with an integral sewing cuff, in accordance with an embodiment.

Referring to FIG. 6A, the fabric 112 was an ePTFE knit tube 176. The ePTFE knit tube 176 was slid over the sacrificial material. Next, a 0.164 mm thick fluoroelastomer film was obtained. The fluoroelastomer was formulated according to the general teachings described in U.S. Pat. No. 7,462,675. A 40 mm wide strip of the fluoroelastomer film 178 was wrapped on top of the knit tube 176, for a total of 1 layer, positioned relative to vent holes 174 as shown in FIG. 6A.

A frame 110 was constructed as follows. The frame 110 was laser machined from a length of seamless MP35N tubing with a wall thickness of 0.60 mm.

Figure 6B:
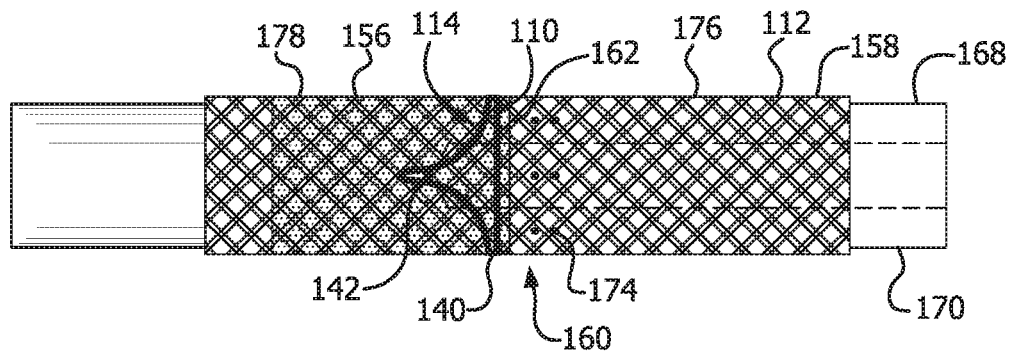

Frame 110 was slid over the fluoroelastomer film 178 and positioned so that the frame base 140 was approximately 1 mm from the edge of fluoroelastomer film 178 as shown in FIG. 6B.

A 40 mm wide strip of the fluoroelastomer film 178 previously described in this example was wrapped on top of the frame 110 and aligned directly above the previously applied fluoroelastomer film 178, for a total of 3 additional layers.

Figure 6C:
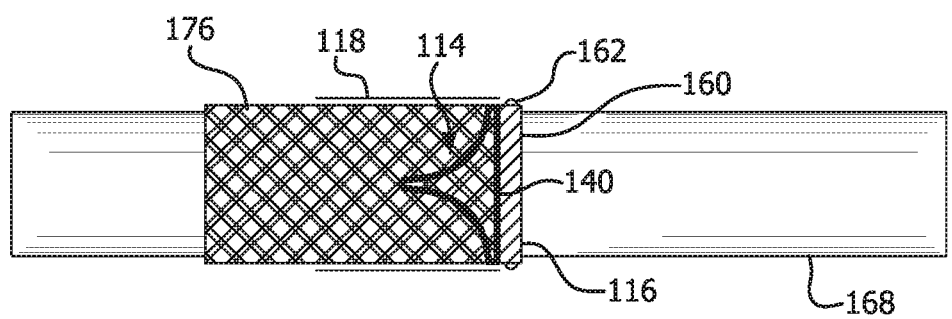

A length of 3.2 mm diameter Gore Joint Sealant (W.L. Gore and Associates, Elkton, Md.) was wrapped around the assembly mandrel, just below the frame base 140 of the frame 110. This material used as filler 162 will provide bulk to the sewing cuff 116 as shown in FIG. 6C.

The excess length of the ePTFE knit tube 176 that is extending beyond the length of the frame 110 was pulled over the filler 162 and the frame 110 so that it extended beyond the frame strut elements 142 of the frame 110.

An ePTFE CV-4 suture was tied around the assembly mandrel 168 and located between the frame base 140 and the filler 162. The suture held the knit in close contact with the frame base 140 and the filler 162.

A 40 mm wide strip of the fluoroelastomer film 178 previously described in this example was wrapped on top of the frame 110 and aligned directly above the previously applied fluoroelastomer film 178, for a total of 14 additional layers.

Two layers of the previously described sacrificial composite material were wrapped on top of the coverings on the frame 110. Adhesive-backed polyimide tape was used to attach the ePTFE/polyimide composite to the assembly mandrel at each end and to seal the longitudinal seam thereby creating a fabric-frame assembly.

The fabric-frame assembly was then placed inside a heated pressure chamber. A vent port 180 in the first end 170 of the assembly mandrel 168 was plumbed to a vacuum source. The fabric-frame assembly was then subjected to 414 KPa pressure for about 26 minutes as the temperature inside the assembly mandrel reached about 260° C.

The pressure vessel was allowed to cool to room temperature. The pressure was released and the assembly mandrel 168 was removed from the pressure vessel. The resulting bonded fabric-frame assembly was slid off of the assembly mandrel 168 and the sacrificial ePTFE/polyimide composite material was removed.

The ePTFE knit tube 176 (the fabric in this embodiment) and fluoroelastomer film 178 of the bonded fabric-frame assembly 1500 was trimmed to within 1 mm of the frame. The fluoroelastomer filled the fabric pores or void spaces within the ePTFE knit in proximity to frame 110, both on the inner fabric frame portion 128 and outer fabric frame portion 132, as shown in FIG. 1C. The fluoroelastomer did not fill the fabric pores within the ePTFE knit and the filler 162 in the fabric central portion 160 of the sewing cuff 116.

Figure 6D:
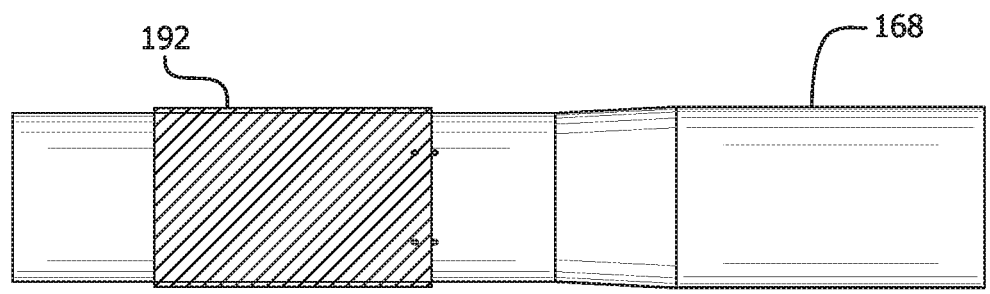

With nothing on the assembly mandrel 168, two layers of the aforementioned sacrificial composite material were wrapped around the assembly mandrel 168 as previously described. The sacrificial composite material was punctured above the vent holes 174. A sacrificial layer of stainless steel foil 192 was wrapped around the assembly mandrel 168, adjacent to and extending away from the row of vent holes 174, as shown in FIG. 6D.

A composite material was then prepared as follows. A membrane layer of ePTFE was manufactured according to the general teachings described in U.S. Pat. No. 7,306,729. The ePTFE membrane was tested in accordance with the methods described herein. The ePTFE membrane had a mass per area of about 1.12 g/m2, a porosity of about 52%, a thickness of about 1.0 µm, a bubble point of about 458 KPa, a matrix tensile strength of about 481 MPa in the longitudinal direction and about 307 MPa in the transverse direction. This membrane was imbibed with the same fluoroelastomer as described previously in this example. The fluoroelastomer was dissolved in Fluorinert Electronic Liquid FC-72, 3M, St. Paul, Minn., USA in an about 3.0% concentration. The solution was coated using a die coater onto the ePTFE membrane (while being supported by a polyethylene release film) and dried in a convection oven set to about 110° C. for about 3 minutes. The resulting composite material of ePTFE/fluoroelastomer had a mass per area of about 3.6 g/m2.

The ePTFE/fluoroelastomer composite material 118 was wrapped around the assembly mandrel 168 and previously applied components for a total of 5 layers. The composite material 118 was trimmed with a razor blade against the sacrificial stainless steel foil, approximately 1 mm from the edge of the foil. The foil and trimmed composite was removed from the assembly mandrel 168.

Figure 6E:
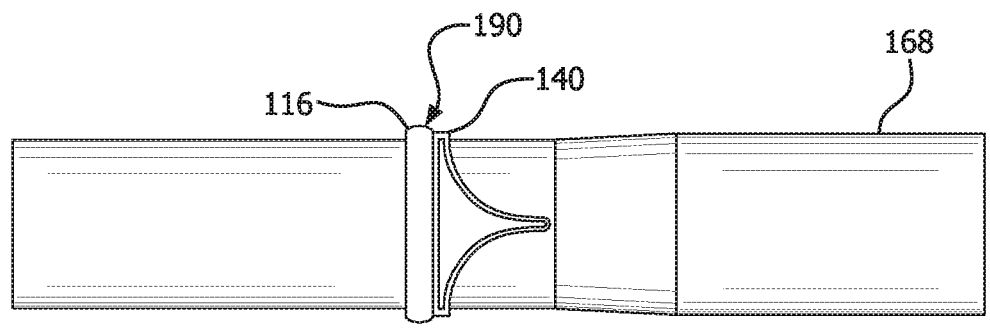

The fabric-frame assembly 190 was slid onto the assembly mandrel 168 and positioned on top of the ePTFE/fluoroelastomer composite material so that the frame base 140 aligned with the edge of the composite material 118 as shown in FIG. 6E.

Figure 6F:
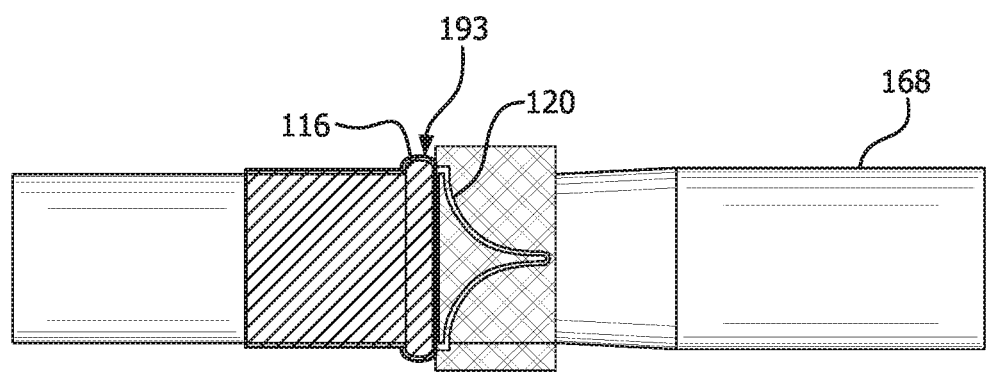

Two layers of the aforementioned sacrificial composite material were wrapped around the fabric-frame assembly so that the edge of the sacrificial composite aligned with the frame base 140 and covered the sewing cuff 116, as shown in FIG. 6F.

Twenty-seven (27) additional layers of the ePTFE/fluoroelastomer composite material 193 were wrapped around the assembly mandrel 168, completely covering all the previously applied components as shown in FIG. 6F.

Two layers of the aforementioned sacrificial composite material were wrapped around the assembly mandrel 168 and previously applied components. Adhesive-backed polyimide tape was used to attach the ePTFE/polyimide composite to the assembly mandrel 168 at each end and to seal the longitudinal seam.

The assembly mandrel 168 with previously applied components was then placed in a pressure vessel and pressurized as described above with the exceptions that the time and temperature were about 24 minutes and 262° C., respectively. This resulting frame assembly 120 with the sewing cuff 116 that is now integral to the frame assembly 120 was allowed to cool to room temperature, removed from the pressure vessel and slid off of the assembly mandrel 168, as shown in FIG. 6F.

The ePTFE/fluoroelastomer composite material was trimmed at the base of the valve frame, revealing the sewing cuff 116 that is still un-imbibed with elastomer.

In subsequent steps, leaflets were attached to the leaflet windows.

Testing Methods

It should be understood that although certain methods and equipment are described below, any method or equipment determined suitable by one of ordinary skill in the art may be alternatively utilized.

Mass, Thickness, and Density of ePTFE Membranes

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho = m/(w*l*t)$, in which: $\rho$=density (g/cm3), m=mass (g), w=width (cm), l=length (cm), and t=thickness (cm). The average of three measurements was reported.

Matrix Tensile Strength (MTS) of ePTFE Membranes

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the Kafer FZ1000/30 snap gauge; alternatively, any suitable means for measuring thickness may be used. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), where the bulk density of the PTFE was taken to be about 2.2 g/cm$^3$. The porosity of the specimen is accounted for by multiplying the tensile strength by the ratio of density of the polymer to the density of the specimen.

Bubble Point and Mean Flow Pore Size

Bubble point and mean flow pore size were measured according to the general teachings of ASTM F31 6-03 using a capillary flow Porometer, Model CFP 1500AEXL from Porous Materials, Inc., Ithaca N.Y., USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. Using the Capwin software version 7.73.012 the following parameters were set as specified in the table below.

| Parameter | Set Point |
| --- | --- |
| Maxflow (cm³/m) | 200000 |
| Bublflow (cm³/m) | 100 |
| F/PT (old bubltime) | 50 |
| Minbpress (PSI) | 0 |
| Zerotime (seconds) | 1 |
| V2incr (cts) | 10 |
| Preginc (cts) | 1 |
| Pulse delay (seconds) | 2 |
| Maxpre (PSI) | 500 |
| Pulse width (seconds) | 0.2 |
| Mineqtime (seconds) | 30 |
| Presslew (cts) | 10 |
| Flowslew (cts) | 50 |

-continued

| Parameter | Set Point |
|---|---|
| Eqiter | 3 |
| Aveiter | 20 |
| Maxpdif (PSI) | 0.1 |
| Maxfdif (PSI) | 50 |
| Sartp (PSI) | 1 |
| Sartf (cm³/m) | 500 |

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed:

1. A method of making a frame assembly for a prosthetic valve, comprising:
coupling a frame defining a tubular shape to a fabric having fabric pores, the fabric defining a fabric frame portion and a sewing cuff portion opposite the fabric frame portion, wherein at least a portion of the fabric frame portion has an elastomer in the fabric pores and the sewing cuff portion of the fabric does not have an elastomer present in the fabric pores; and
coupling a composite material to at least a portion of the fabric frame portion with the fabric frame portion disposed between the frame and the composite material and such that the sewing cuff extends from the frame.

2. The method of claim 1, further comprising:
wrapping a first layer of film into a tubular form about a mandrel;
placing the fabric partially over the first layer of film;
placing the frame over the fabric that is over the first layer of film;
everting the fabric over the frame to define a fold in the fabric with the fold, the fold defining the sewing cuff at a base of the frame;
wrapping a second layer of film over the frame; and
coupling the first layer of film and the second layer of film to each other, to the fabric, and to the frame.

3. The method of claim 2, further comprising providing filler material in the fold of the fabric, wherein after everting the fabric the filler material is contained within the fold.

4. The method of claim 2, further comprising coupling one or more leaflets to the frame.

5. The method of claim 2, the frame further comprising two or more frame strut elements extending from the base to define a plurality of leaflet windows.

6. The method of claim 5, wherein one or more of the first layer of film and the second layer of film extends into each of the leaflet windows to define leaflets therein.

7. The method of claim 2, wherein the frame has a frame inside surface and a frame outside surface opposite the frame inside surface, the fabric frame portion being coupled to the frame inside surface, the fabric frame portion disposed between the frame inside surface and the composite material.

8. The method of claim 2, wherein the frame has a frame inside surface and a frame outside surface opposite the frame inside surface, the fabric frame portion being coupled to the frame inside surface and the frame outside surface, the fabric frame portion disposed between the frame inside surface and the composite material, and the fabric frame portion disposed between the frame outside surface and the composite material.

* * * * *